(12) United States Patent
Zhang et al.

(10) Patent No.: US 7,671,258 B2
(45) Date of Patent: *Mar. 2, 2010

(54) SURFACTANT PEPTIDE NANOSTRUCTURES, AND USES THEREOF

(75) Inventors: Shuguang Zhang, Lexington, MA (US); Sylvain Vauthey, Morges (CH)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/338,987

(22) Filed: Jan. 25, 2006

(65) Prior Publication Data

US 2006/0211615 A1    Sep. 21, 2006

Related U.S. Application Data

(63) Continuation of application No. 10/192,832, filed on Jul. 10, 2002.

(60) Provisional application No. 60/304,256, filed on Jul. 10, 2001.

(51) Int. Cl.
C07K 4/00 (2006.01)
C07K 19/00 (2006.01)
A61K 38/00 (2006.01)

(52) U.S. Cl. ............... 977/705; 514/13; 514/14; 514/15; 514/16; 530/300; 530/324; 530/326

(58) Field of Classification Search .......... 514/2; 530/300
See application file for complete search history.

(56) References Cited

U.S. PATENT DOCUMENTS

| | | | |
|---|---|---|---|
| 5,440,016 A | | 8/1995 | Blondelle et al. |
| 5,698,673 A | * | 12/1997 | Blondelle et al. ........... 530/329 |
| 5,854,204 A | | 12/1998 | Findeis et al. |
| 5,955,343 A | | 9/1999 | Holmes et al. |
| 5,985,242 A | * | 11/1999 | Findeis et al. ................ 424/9.1 |
| 6,201,065 B1 | | 3/2001 | Pathak et al. |
| 6,428,811 B1 | | 8/2002 | West et al. |

FOREIGN PATENT DOCUMENTS

| | | |
|---|---|---|
| EP | 0401177 | 12/1990 |
| JP | 09157297 | 6/1997 |
| WO | WO 91/18016 | 11/1991 |
| WO | WO 93/24525 | 12/1993 |
| WO | WO 94/18345 | 8/1994 |
| WO | WO 95/07093 | 3/1995 |
| WO | WO 95/24419 | 9/1995 |
| WO | WO 96/11942 | 4/1996 |

OTHER PUBLICATIONS

Misicka et al. (1995) Amino acids with amphiphilic side chains: Deltorphin analogues with Phe3 replaced by all β-hydroxyphenylalanine diastereoisomers, Lett. Peptide Science, vol. 2, pp. 203-205.*

ANASPEC (2007, updated) Unusual amino acids, http://www.anaspec.com/products/product.asp?id=41099, pp. 1-3.*

Wagner et al. (2005) "Toward the development of peptide nanofilaments and nanoropes as smart materials", Proc. Natl. Acad. Sci. U S A., vol. 102, No. 36, pp. 12656-12661.*

Hendrickson et al. (2004) "Incorporation of nonnatural amino acids into proteins", Annu. Rev. Biochem., vol. 73, pp. 147-176.*

Caplan, et al., "Control of Self-Assembling Oligopeptide Matrix Formation Through Systemic Variation of Amino Acid Sequence," *Biomaterials*, 23: 219-227 (2002).

International Search Report Completed on Aug. 28, 2002 and Mailed on Sep. 19, 2002.

Aggeli, et al., "Responsive Gels Formed by the Spontaneous Self-Assembly of Peptided into Polymeric β-Sheet Tapes," *Nature*, 286: 259-262 (Mar. 20, 1997).

Baker and DeGrado, "Engineering and Design," *Current Opinion in Structural Biology*, 9: 485-486 (1999).

Bieri et al., "Micropatterned Immobilization of G Protein-Coupled Receptor and Direct Detection of G Protein Activation," *Nature Biotechnology*, 17: 1105-1108 (Nov. 1999).

Bong et al., "Self Assembling Organic Nanotubes," *Angew. Chem. Int. Ed.*, 40: 988-1011 (2001).

Cates, E.M., "Reptation of Living Polymers: Dynamics of Entangled Polymer in the Presence of Reversible Chain-Scission Reactions," *Macromolecules*, 20: 2289-2296 (1987).

Cates, E.M., "Dynamics of Living Polymers and Flexible Surfactant Micelles: Scaling Laws for Dilution," *J. Phys. France*, 49: 1593-1600 (1988).

Drye and Cates, "Statics and Dynamics of Self-Assembled Dipolar Rods," *J. Chem. Phys.*, 98(12): 9790-9797 (Jun. 15, 1993).

Ghadiri et al., "Artificial Transmembrane Ion Channels from Self-Assembling Dipolar Rods," *Nature*, 369: 301-304 (May 26, 1994).

Hassan and Yakhmi, "Growth of Cationic Micelles in the Presence of Organic Additives," *Langmuir*, 16: 7187-7191 (2000).

Hubbell A. Jeffrey, "In Situ Material Transformation in Tissue Engineering," *MRS Bulletin*, 21(11): 33-35 (1996).

Hecht, et al., "De Novo Design, Expression and Characterization of Felix: A Four-Felix Bundle Protein of Native-Like Sequence," *Science*, 249: 884-891 (Aug. 1990).

Hol, et al., "Dipoles of the α-helix and β-sheet: Their role in Protein Folding," *Nature*, 294: 532-536 (1981).

(Continued)

*Primary Examiner*—Jon P Weber
*Assistant Examiner*—Samuel W Liu
(74) *Attorney, Agent, or Firm*—Elmore Patent Law Group; Carolyn S. Elmore; Mahreen Chaudhry Hoda

(57) ABSTRACT

This work describes a new class of short polypeptides that can self-assemble to form regular nanotubes with an average diameters of about 50 nm. These peptides (7 to 8 amino acids) have a structure very similar to those observed in surfactant molecules with a defined hydrophilic head group constituting of charged amino acids and a lipophilic tail made out of hydrophobic amino acids such as alanine, valine or leucine. Cryo-TEM micrographs show numerous three-fold junctions connecting the self-assembling nanostructures and thus leading to the formation of a rather dense network of entangled nanotubes. Additionally, the observation of clear openings at the end of the supramolecular structures confirms the presence of tubular organization.

48 Claims, 5 Drawing Sheets

OTHER PUBLICATIONS

Israwlachvili et al., "Theory of Self-Assembly of Hydrocarbon Amphiphiles into Micelles and Bilayers," *J. Chem. Soc. Faraday Trans. II*, 72: 1525-1568 (1976).

Langer and Vacanti, "Tissue Engineering," *Science*, 260: 920-926 (1993).

Leon et al., "Mechanical Properties of a Self-Assembling Oligopeptide Matrix," *J. Biomater. Sci. Polymer Edn.*, 9(3): 297-312 (1998).

Magid, J.E., "The Surfactant-Polyelectrolyte Analogy," *J. Phys. Chem. B.*, 102: 4064-4074 (1998).

Minor, Jr. and Kim, "Context-Dependent Secondary Structure Formation of a Designed Protein Sequence," *Nature*, 380: 730-734 (1996).

Nemoto, et al., "Dynamic Light Scattering of CTAB/NaSal Thread-like Micelles in a Semidilute Regime. 3. Dynamical Coupling Between Concentration Fluctuation and Stress," *Langmuir*, 11: 30-36 (1995).

O'Shea et al., "Evidence that Lecine Zipper is a Coiled Coil," *Science*, 243: 538-542 (1989).

Schnur M. Joel, "Lipid Tubules: A Paradigm for Molecularly Engineered Structures," *Science*, 262: 1669-1676 (1993).

Selinger et al., "Theory of Cylindrical Tubules and Helical Ribbons of Chiral Lipid Membranes," *Phys. Rev. E.*, 53(4): 3804-3818 (1996).

Slichipunov A. Yu, "Growth, Branching and Local Ordering of Lecithin Polymer-Like Micelles," *Langmuir*, 14: 6350-6360 (1998).

Shikata and Imai, "Entanglements in a Threadlike Micellar System as Studied by Dielectric Relaxation," *Langmuir*, 16: 4840-4845 (2000).

Takahashi et al., "Optimization of Hydrophobic Domains in Peptides That Undergo Transformation from α-Helix to β-Fibril," *Bioorganic & Medicinal Chemistry*, 7: 177-185 (1999).

Tan and Richmond, "Crystal Structure of the Yeast MAT α2/MCM1/DNA ternary Complex," *Nature*, 391: 660-666 (1998).

Whitesides et al., "Molecular Self-Assembly and Nanochemistry: A Chemical Strategy for the Synthesis of Nanostructures."

Zhang et al., "Spontaneous Assembly of a Self-Complementary Oligopeptide to Form a Stable Macroscopic Membrane," *Proc. Natl. Acad. Sci. USA*, 90: 3334-3338 (1993).

Zhang et al., "Direct Conversion of An Oligopeptide from a β-Sheet to an α-Helix: A Model for Amyloid Formation," *Proc. Natl. Acad. Sci. USA*, 94: 23-28 (1993).

Zhang et al., "Unusually Stable β-Sheet Formation in an Ionic Self-Complementary Oligopeptide," *Biopolymers*, 34: 663-672 (1994).

Zhang et al., "Self-Complementary Oligopeptide Matrices Support Mammalian Cell Attachment," *Biomaterials*, 16: 1385-1393 (1995).

Zhang et al., "Biological Surface Engineering: A Simple System for Cell Pattern Formation," *Biomaterials*, 20: 1213-1220 (1999).

Nguyen, J.T. et al., "Exploiting the Basis of Proline Recognition by SH3 and WW domains: Design of N-Substituted Inhibitors," *Science*, 282: 2088-2092 (1998).

Ranganathan, D., et al., "Self-Assembling, Cystine-Derived, Fused Nanotubes Based on Spirane Architecture: Design, Synthesis, and Crystal Structure of Cystinospiranes," *J. Am. Chem. Soc.*, 123: 5619-5624 (2001).

Crump, M.P., et al., "Solution Structure and Basis for Functional Activity of Stromal Cell-Derived Factor-1; Dissociation of CXCR4 Activation from Binding and Inhibition of HIV-1," *EMBO J.*, 16: 6996-7007 (1997).

Cardinaux, F., et al., "Block Copolymers of Amino Acids. I. Synthesis and Structure of Copolymers and L-Alanine or L-Phenylalanine with D,L-Lysine-$d_7$ or D,L-Lysine," *Biopolymers*, 16: 2005-2028 (1977).

Vitello, L., et al., "Block Poly(Ala)-Poly(Lys). A Water-Soluble Model for Intrinsic Membrane Proteins?," *Biochimica et Biophysica Acta*, 557: 331-339 (1979).

Hayashi, T., et al., "Block Copolypeptides. 1. Synthesis and Solid State Conformational Studies," *Macromolecules*, 10(2):346-351 (1977).

Vila, J., et al., "The intrinsic helix-forming tendency of L-alanine," *Proc. Natl. Acad. Sci. USA*, 89:7821-7825 (1992).

Vila, J., et al., "Influence of Lysine Content and pH on the Stability of alanine-Based Copolypeptides," *Biopolymers*, 58:235-246 (2001).

Whitesides et al., "Molecular Self-Assembly and Nanochemistry: A Chemical Strategy for the Synthesis of Nanostructures," *Science*, 254: 1312-1319 (1991).

\* cited by examiner

SURFACTANT PEPTIDE NANOSTRUCTURES, AND USES THEREOF

RELATED APPLICATIONS

This application is a continuation of U.S. application Ser. No. 10/192,832, filed Jul. 10, 2002, which claims the benefit of U.S. Provisional Application No. 60/304,256, filed on Jul. 10, 2001. The entire teachings of the above application(s) are incorporated herein by reference.

GOVERNMENT SUPPORT

This invention was made with government support under Grant Number 1R01GM55781, awarded by the National Institutes of Health; therefore, the government has certain rights in the invention.

FIELD OF THE INVENTION

The invention relates to dipolar oligopeptides that self assemble to form very regular structures. The invention also relates to methods of forming gold nanostructures by localizing gold upon the self assembled structures of the present invention. The invention also relates to methods of delivering drugs and other guest compounds across a host membrane using the self assembled structures of the present invention. The invention also relates to filtration systems based on nanotubes of the present invention. The invention also relates to pharmaceutical compositions comprising a compound of the present invention.

BACKGROUND OF THE INVENTION

Molecular self-assembly is the spontaneous organization of molecules into structurally well-defined arrangements due to non-covalent interactions. The resulting supramolecular structure usually provides nanoarchitectures with very defined macroscopic properties[1]. As a result, molecular assemblies have attracted much attention in relation to the development of novel materials. In the last decade, molecular self-assembly of biopolymer has shown to play a key role in the discovery and design of biomaterials finding applications in the field of medical technology such as, e.g., regenerative medicine and drug delivery systems[2,3]. Recently, among the different systems investigated, a new class of ionic self-complementary oligopeptide has attracted a great deal of attention due to their ability to spontaneously self-assemble to form stable macroscopic structure in the presence of monovalent cations[4].

A number of peptide molecular self-assembly systems have been designed and developed (Table 1). This systematic analysis provided insight into the chemical and structural principles of peptide self-assembly. These peptides are short, simple to design, extremely versatile and easy to synthesize. Three types of self-assembling peptides have been systematically studied thus far. It is believed additional different types will be discovered and developed in the coming years. This class of biological materials has considerable potential for a number of applications, including scaffolding for tissue repair and regenerative medicine, drug delivery of molecular medicine, as well as biological surface engineering. Similar systems have also been described where these peptide systems undergo self-assembly to form gel with regular β-sheet tapes of well-defined structures[5]. The self-assembly of peptide nanotubes that allow ions to pass through and to insert themselves into lipid bilayer membrane were also described[6,7]. Furthermore a number of fascinating biomimetic peptide and protein structures have been engineered, such as helical coil-coils, di-, tri- and tetra-helical bundles[8,10]. However, their applications for materials science and engineering remain under explored. It is likely that these stable coiled coils will be developed as nanomaterials in the future.

Type I Self-assembling Peptides

Type I peptides, also called "molecular Lego", form β-sheet structures in aqueous solution because they contain two distinct surfaces, one hydrophilic, the other hydrophobic. See U.S. Pat. No. 5,670,483. Like Lego bricks that have pegs and holes and can only be assembled into particular structures, these peptides can do so at the molecular level. The unique structural feature of these peptides is that they form complementary ionic bonds with regular repeats on the hydrophilic surface. The complementary ionic sides have been classified into several moduli, i.e. modulus I, II, III, IV, etc., and mixed moduli. This classification is based on the hydrophilic surface of the molecules that have alternating + and − charged amino acid residues, either alternating by 1, 2, 3, 4 and so on. For example, molecules of modulus I have − + − + − +, modulus II, − − + + − − + +, modulus IV − − − − + + + +. These well defined sequences allow them to undergo ordered self-assembly, resembling some situations found in well studied polymer assemblies.

Upon the addition of monovalent alkaline cations or the introduction of the peptide solutions into physiological media, these oligopeptides spontaneously assemble to form macroscopic structures that can be fabricated into various geometric shapes[11]. Scanning EM reveals that the matrices are made of interwoven filaments that are about 10-20 nm in diameter and pores about 50-100 nm in diameter[12,13].

The molecular structure and proposed complementary ionic pairings of the Type I peptides between positively charged lysines and negatively charged glutamates in an overlap arrangement represent an example of this class of self-assembling β-sheet peptides that spontaneously undergo association under physiological conditions. If the charged residues are substituted, i. e., the positive charged lysines are replaced by positively charged arginines and the negatively charged glutamates are replaced by negatively charged aspartates, there are essentially no drastic effects on the self-assembly process. However, if the positively charged resides, Lys and Arg are replaced by negatively charged residues, Asp and Glu, the peptide can no longer undergo self-assembly to form macroscopic materials although they can still form β-sheet structures in the presence of salt. If the alanines are changed to more hydrophobic residues, such as Leu, Ile, Phe or Tyr, the molecules have a greater tendency to self-assemble and form peptide matrices with enhanced material strength[13].

A number of mammalian cells have been tested and all have been found to be able to form stable attachments with the peptide materials[11]. Several peptide materials have been used to test for their ability to support cell proliferation and differentiation. These results suggested that the peptide materials can not only support various types of cell attachments, but can also allow the attached cells to proliferate and differentiate. For example, rat PC12 cells on peptide matrices were exposed to Nerve Growth Factor (NGF), they underwent differentiation and exhibited extensive neurite outgrowth. In addition, when primary mouse neuron cells were allowed to attach the peptide materials, the neuron cells projected lengthy axons that followed the specific contours of the self-assembled peptide surface.

The fundamental design principles of such self-assembling peptide systems can be readily extended to polymers and polymer composites, where co-polymers can be designed and produced.

Type II Self-assembling Peptides

Several Type II peptides are developed as "Molecular Switches" in which the peptides can drastically change its molecular structure. One of the peptides with 16 amino acids, DAR16-IV, has a β-sheet structure at ambient temperature with 5nm in length but can undergo an abrupt structural transition at high temperatures to form a stable α-helical structure with 2.5 nm length[14]. Similar structural transformations can be induced by changes of pH. This suggests that secondary structures of some sequences, especially segments flanked by clusters of negative charges on the N-terminus and positive charges on the C-terminus, may undergo drastic conformational transformations under the appropriate conditions. These findings can not only provide insights into protein-protein interactions during protein folding and the pathogenesis of some protein conformational diseases, including scrapie, Huntington's, Parkinson's and Alzheimer's disease, but also can be developed as molecular switches for a new generation of nanoactuators.

The peptides of DAR16-IV (DADADADARARARARA) (SEQ ID NO: 30) and EAK12 (AEAEAEAEAKAK) (SEQ ID NO: 22) have a cluster of negatively charged glutamate residues close to N-terminus and a cluster of positively charged Arg residues near C-terminus. It is well known that all α-helices have a helical dipole moment with a partial negative C-terminus toward a partial positive N-terminus[15]. Because of the unique sequence of DAR16-IV and EAK12, their side chain charges balance the helical dipole moment, therefore favoring helical structure formation. However, they also have alternating hydrophilic and hydrophobic residue as well ionic self-complementarity, which have been previously characterized to form stable β-sheets. Thus the behavior of this Type II of molecules is likely to be more complex and dynamic than other stable β-sheet peptides. Additional molecules with such dipoles have been designed, studied and confirmed the initial findings.

Others have also reported similar findings that proteins and peptides can undergo self-assembly and disassembly or change their conformations depending on the enviromnental influence, such as its location, pH change and temperature or crystal lattice packing[16,18].

Type III Self-assembling Peptides

Type III peptides, like "Molecular Paint" and "Molecular Velcro"; undergo self-assembly onto surface rather with among themselves. They form monolayers on surfaces for specific cell pattern formation or to interact with other molecules. These oligopeptides have three distinct features. The first feature is the terminal segment of ligands that incorporate a variety of functional groups for recognition by other molecules or cells. The second feature is the central linker where a variable spacer is not only used to allow freedom of interaction at a specified distance away from the surface but also permit the flexibility or rigidity. The third feature is the surface anchor where a chemical group on the peptide can react with the surface to form a covalent bond. This simple system using Type III self-assembly peptides and other substances to engineer surfaces is an emerging technology that will be a useful tool in biomedical engineering and biology. This biological surface engineering technique will provide new methods to study cell-cell communication and cell behavior[19].

Other previously pioneered molecular self-assembly systems through the incorporation of organic linkers for surface anchoring have been developed by George Whitesides and his colleagues[1].

TABLE 1

Type I self-assembling peptides studied.

| Name | Sequence (N→C) | Ionic +Modulus | Structure |
|---|---|---|---|
| RADA16-I (SEQ ID NO: 1) | + - + - + - + -<br>n-RADARADARADARADA-c | I | β |
| RGDA16-I (SEQ ID NO: 2) | + - + - + - + -<br>n-RADARGDARADARGDA-c | I | r.c. |
| RADA8-I (SEQ ID NO: 3) | + - + -<br>n-RADARADA-c | I | r.c. |
| RAD16-II (SEQ ID NO: 4) | + + - - + + - -<br>n-RARADADARARADADA-c | II | β |
| RAD8-II (SEQ ID NO: 5) | + + - -<br>n-RARADADA-c | II | r.c. |
| EAKA16-I (SEQ ID NO: 6) | - + - + - + - +<br>n-AEAKAEAKAEAKAEAK-c | I | β |
| EAKA8-I (SEQ ID NO: 7) | - + - +<br>n-AEAKAEAK-c | I | r.c. |
| RAEA16-I (SEQ ID NO: 8) | + - + - + - + -<br>n-RAEARAEARAEARAEA-c | I | β |
| RAEA8-I (SEQ ID NO: 9) | + - + -<br>n-RAEARAEA-c | I | r.c. |
| KADA16-I (SEQ ID NO: 10) | + - + - + - + -<br>n-KADAKADAKADAKADA-c | I | β |
| KADA8-I (SEQ ID NO: 11) | + - + -<br>n-KADAKADA-c | I | r.c. |
| EAH16-II (SEQ ID NO: 12) | - - + + - - + +<br>n-AEAEAHAHAEAEAHAH-c | II | β |
| EAH8-II (SEQ ID NO: 13) | - - + +<br>n-AEAEAHAH-c | II | r.c. |
| EFK16-II (SEQ ID NO: 14) | - - + + - - + +<br>n-FEFEFKFKFEFEFKFK-c | II | β |

TABLE 1-continued

Type I self-assembling peptides studied.

| Name | Sequence (N→C) | Ionic +Modulus | Structure |
|---|---|---|---|
| EFK12-I (SEQ ID NO: 15) | n-FEFKFEFKFEFK-c  (− + − + − + − +) | I | β |
| EFK8-II (SEQ ID NO: 16) | n-FEFKFEFK-c  (− + − +) | I | β |
| ELK16-II (SEQ ID NO: 17) | n-LELELKLKLELELKLK-c  (− − + + − − + +) | II | β |
| ELK8-II (SEQ ID NO: 18) | n-LELELKLK-c  (− − + +) | II | β |
| EAK16-II (SEQ ID NO: 19) | n-AEAEAKAKAEAEAKAK-c  (− − + + − − + +) | II | β |
| EAK12 (SEQ ID NO: 20) | n-AEAEAEAEAKAK-c  (− − − − + +) | IV/II | α/β |
| EAK8-II (SEQ ID NO: 21) | n-AEAEAKAK-c  (− − + +) | II | r.c. |
| KAE16-IV (SEQ ID NO: 22) | n-KAKAKAKAEAEAEAEA-c  (+ + + + − − − −) | IV | β |
| EAK16-IV (SEQ ID NO: 23) | n-AEAEAEAEAKAKAKAK-c  (− − − − + + + +) | IV | β |
| KLD12-I (SEQ ID NO: 24) | n-KLDLKLDLKLDL-c  (+ − + − + −) | I | β |
| KLE12-I (SEQ ID NO: 25) | n-KLELKLELKLEL-c  (+ − + − + −) | I | β |
| RAD16-IV (SEQ ID NO: 26) | n-RARARARADADADADA-c  (+ + + + − − − −) | IV | β |
| DAR16-IV (SEQ ID NO: 27) | n-ADADADADARARARAR-c  (− − − − + + + +) | IV | α/β |
| DAR16-IV* (SEQ ID NO: 28) | n-DADADADARARARARA-c  (− − − − + + + +) | IV | α/β |
| DAR32-IV (SEQ ID NO: 29) | n-(ADADADADARARARAR)-c  (− − − − + + + +) | IV | α/β |
| EHK16 (SEQ ID NO: 30) | n-HEHEHKHKHEHEHKHK-c  (+ − + − + + + + + − + − + + + +) | N/A | r.c. |
| EHK8-I (SEQ ID NO: 31) | n-HEHEHKHK-c  (+ − + − + + + +) | N/A | r.c. |
| VE20* (SEQ ID NO: 32) | n-VEVEVEVEVEVEVEVEVEVE-c  (− − − − − − − − − −) | N/A | β (NaCl) |
| RF20* (SEQ ID NO: 33) | n-RFRFRFRFRFRFRFRFRFRF-c  (+ + + + + + + + + +) | N/A | β (NaCl) |

β, β-sheet; α, α-helix; r.c., random coil; N/A, not applicable. The numbers follow the name denote the length of the peptides.
*Both VE20 and RF20 are in β-sheet form when they are incubated in solution containing NaCl. They do not self-assemble to form macroscopic matrices.

In another attempt to exploit the intrinsic self-assembly of polypeptides as a new avenue to supramolecular materials, Aggeli et al. have designed different short oligopeptides that self-assemble, in non-aqueous solvent, into long, semi-flexible, polymeric β-sheet nanoptapes[5]. These systems were rationally designed to provide strong cross-strands attractive forces between the side chains such as electrostatic interactions, hydrophobic interactions or hydrogen-bondings. In another study, Ghadiri and co-workers have produced self-assembling nanotubes made from cyclic D,L-α-peptides and cyclic β-peptide. They first showed the evidence that D,L-cyclic peptide subunits (cyclo[-(L-Gln-D-Ala-L-Glu-D-Ala)$_2$-]) (SEQ ID NO: 34) adopt flat, ring-shaped conformations and stack through backbone-backbone hydrogen bonding to form extended cylindrical structures[20].

SUMMARY OF THE INVENTION

The present invention describes a new type of short oligopeptides and di- and tri-block peptide copolymers whose properties closely mimic those found in surfactant molecules. The objective being to form new self-assembled nanostructures, very similar to those observed in surfactant solutions. It is well known that most surfactants are amphiphilic molecules that tend to aggregate in order to isolate the hydrocarbon chain from the contact with water. The common feature for this self-association is the formation of a polar interface, which separates the hydrocarbon and water regions. Perhaps the most common structure formed in water is the spherical micelle consisting of typically 50-100 lipid molecules arranged so that their hydrocarbon tails form the interior of the micelle, and the polar head groups act as a shield against the surrounding water. The micelle, however, is only one of many aggregate types formned. Depending on the surfactant and its concentration, various structures are found, including liposomes, lamellar phase, hexagonal and cubic structures. Among the latter, liposomes have attracted a particular interest due to its potential utility for conventional drug delivery.

The initial results based on the self-assembly of short amphiphilic peptides have shown very defined structures of about 50 nm. It has also been observed that these self-assembled structures can be modified by external parameters such as pH. Moreover, an adequate design of the peptide allows fine-tuning the self-assemblies properties, giving a high flexibility for various potential applications. Regarding these different issues, the development of controllable and reproducible liposomal systems for systematic drug delivery system has been relatively ineffective. In this context, it is strongly believed that structures based on oligopeptides self-assemblies may have the ability to entrap and deliver molecules with a high degree of efficiency and thus could open innovative avenues for novel drug/gene delivery systems.

In certain embodiments, the compounds of the present invention are represented by the following formnulas:

| Sequence (N → C) | Formula |
|---|---|
| $(\phi)_m(+)_n$ | 1 |
| $(+)_n(\phi)_m$ | 2 |
| $(\phi)_m(-)_n$ | 3 |
| $(-)_n(\phi)_m$ | 4 |
| $(-)_n(\phi)_m(-)_n$ | 5 |
| $(+)_n(\phi)_m(+)_n$ | 6 |
| $(\phi)_m(-)_n(\phi)_m$ | 7 |
| $(\phi)_m(+)_n(\phi)_m$ | 8 |
| $(+)_n(\phi)_m(-)_n$ | 9 |
| $(-)_n(\phi)_m(+)_n$ | 10 | wherein ($\phi$) represents amino acids, natural or non-natural, containing nonpolar, noncharged sidechains;

(+) represents amino acids, natural or non-natural, containing cationic sidechains at physiological pH;

(−) represents amino acids, natural or non-natural, containing anionic sidechains at physiological pH;

m represents an integer >5; and n represents an integer >1.

In certain embodiments, the present invention provides self-assembled structures comprising compounds of formulas 1-10.

DETAILED DESCRIPTION OF THE INVENTION

Figure 1:
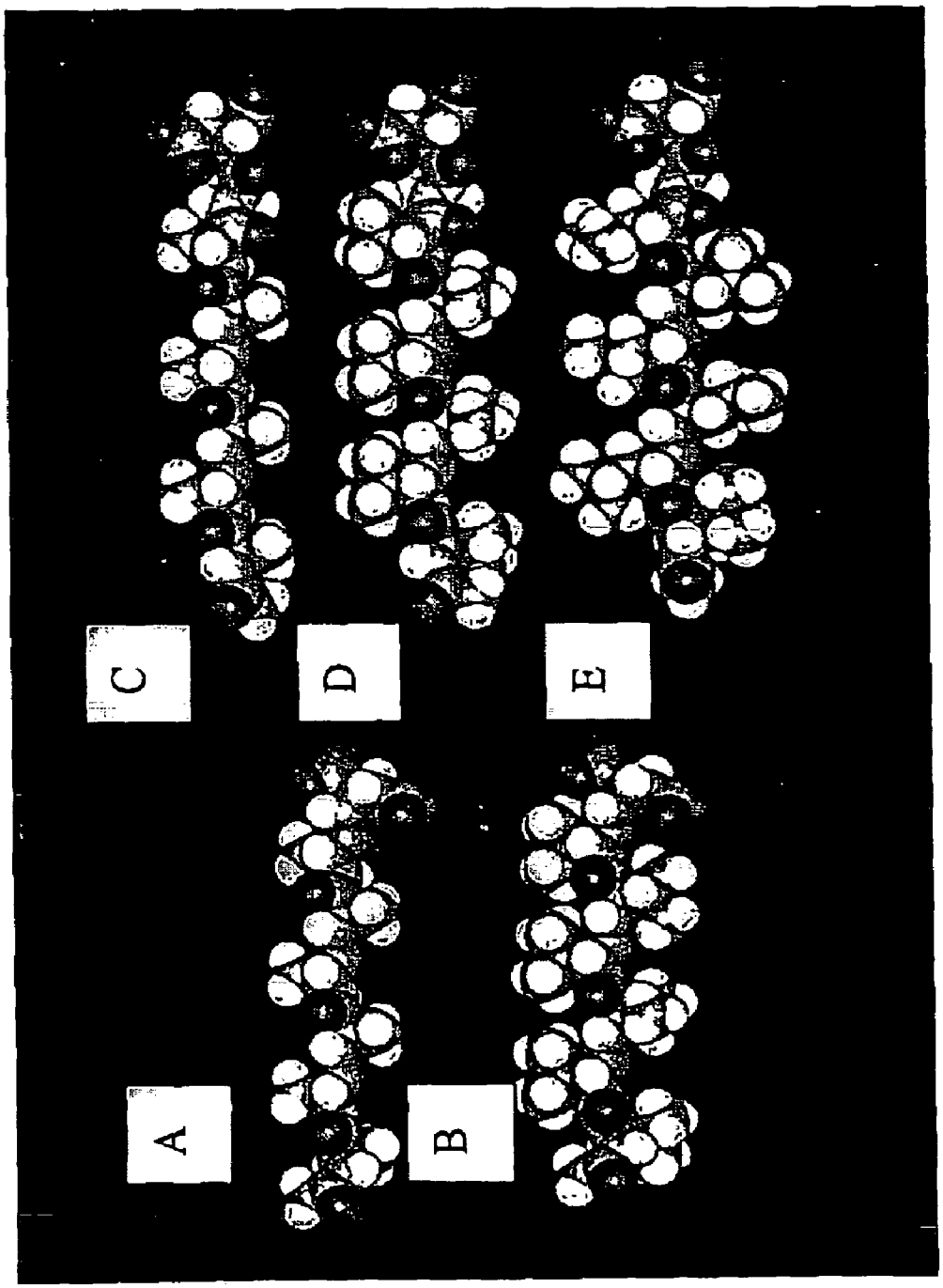
FIG. 1 depicts molecular models of surfactant peptide monomers. A) AAAAAAD ($A_6D$) (SEQ ID NO: 35); B) VVVVVVD ($V_6D$) (SEQ ID NO: 36); C) AAAAAADD ($A_6D_2$) (SEQ ID NO: 37); D) VVVVVVDD ($V_6D_2$) (SEQ ID NO: 38); and E) LLLLLLDD ($L_6D_2$) (SEQ ID NO: 39) (See Table 1).

The present invention aims to describe the extraordinary self-assembly behavior of a new type of surfactant-like peptides. This class of peptides has been designed and investigated for their ability to spontaneously self-assemble to form stable nanotubes. These short peptides (7 to 8 amino acids) have a structure very similar to those observed in surfactant molecules with a defined hydrophilic head group constituted of charged amino acids and a lipophilic tail made out of hydrophobic amino acids such as alanine, valine, isoleucine or leucine. As a result, when dispersed in water, the amphiphilic peptides tend to self-assemble in order to isolate the hydrophobic tail from the contact with water. The common feature for this self-assembly is the formation of a polar interface, which separates the hydrocarbon and water regions.

Definitions

For convenience, certain terms employed in the specification, examples, and appended claims are collected here.

The amino acids will be represented by their commonly assigned letter designations:

A for alanine, C for cysteine, D for aspartic acid, E for glutamic acid, F for phenylalanine, G for glycine, H for histidine, I for isoleucine, K for lysine, L for leucine, M for methionine, N for asparagine, P for proline, Q for glutamine, R for arginine, S for serine, T for threonine, V for valine, W for tryptophan, and Y for tyrosine.

The term "amphiphilic" refers to a molecule which has a polar head attached to a long hydrophobic tail, or a molecule that has a polar segment and a nonpolar segment.

The term "axial ratio" refers to the ratio of the length of the self assembled structure to one of the lateral axes taken as unity.

The term "cryo-transmission electron microscopy" refers to a form of microscopy done at low temperatures, usually at −160° C. to −50° C., where the specimen transmits an electron beam focused on it, image contrasts are formed by the scattering of electrons out of the beam, and various magnetic lenses perform functions analagous to those of ordinary lenses in a light microscope.

The term "hydrogel" refers to the formation of a colloid in which the disperse phase (colloid) has combined with the continuous phase (water) to produce a viscous jellylike product.

The term "hydrophilic" refers to having an affinity for, attracting, adsorbing, or absorbing water.

The term "hydrophobic" refers to lacking an affinity for, repelling, or failing to adsorb or absorb water.

The term "lamellar phase" refers to one of the possible structures formed by a surfactant depending on the surfactant and its concentration characterized by a thin plate-like shape.

The term "lecithin" refers to any group of phospholipids having the general composition $CH_2OR_1CH_2OR_2CH_2OPO_2OHR_3$, in which $R_1$ and $R_2$ are fatty acids and $R_3$ is choline, and with emulsifying, wetting, and antioxidant properties.

The term "lipophilic" refers to having a strong affinity for fats.

The term "liposome" refers to one of the fatty droplets occurring in the cytoplasm.

The term "micelle" refers to a colloidal aggregate of a unique number (between 50 and 100) of amphiphilic moledules.

The term "nanotube" refers to a hollowed out cylindrically shaped formation of atoms, molecules, or peptides of any length but with a diameter on the nanometer scale.

The term "neurite outgrowth" refers to the outgrouth of nerve fiber of a neuron that carries the unidirectional nerve impulse away from the cell body.

The term "oligopeptide" refers to a peptide composed of no more than 10 amino acids.

The term "physiological pH" refers to a pH of about 7.

The term "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P.G.M. *Protective Groups in Organic Synthesis*, $2^{nd}$ ed.; Wiley: N.Y., 1991).

The term "pKa" refers to the negative logarithm of the acid equilibrium constant. The lower the pKa the more acidic the acid is.

The term "self assembly" refers to the process of atoms, molecules, or peptides to form regular shaped structures in response to the general conditions of their environment.

Compounds of the Invention

In certain embodiments, the compounds of the present invention are represented by formulas 1-10:

| Sequence (N → C) | Formula |
|---|---|
| $(\phi)_m(+)_n$ | 1 |
| $(+)_n(\phi)_m$ | 2 |
| $(\phi)_m(-)_n$ | 3 |
| $(-)_n(\phi)_m$ | 4 |
| $(-)_n(\phi)_m(-)_n$ | 5 |
| $(+)_n(\phi)_m(+)_n$ | 6 |
| $(\phi)_m(-)_n(\phi)_m$ | 7 |
| $(\phi)_m(+)_n(\phi)_m$ | 8 |
| $(+)_n(\phi)_m(-)_n$ | 9 |
| $(-)_n(\phi)_m(+)_n$ | 10 | wherein ($\phi$) represents independently for each occurrence a natural or non-natural amino acid comprising a nonpolar, non-charged sidechain;

(+) represents independently for each occurrence a natural or non-natural amino acid comprising a sidechain that is cationic at physiological pH;

(−) represents independently for each occurrence a natural or non-natural amino acid comprising a sidechain that is anionic at physiological pH;

m represents an integer greater than or equal to 5; and n represents an integer greater than or equal to 1.

In certain embodiments, the compounds of formulas 5-10 are tri-block peptide co-polymers.

In certain embodiments, the present invention provides self assembled structures from compounds of formulas 1-10.

In certain embodiments, the present invention provides gold nanostructures formed by localizing gold upon the self assembled structures of the present invention.

In certain embodiments, the present invention provides a method of delivering guest compounds across a host membrane comprising the step of administering the guest compound within the self assembled structures of the present invention.

In certain embodiments, the present invention provides a method of delivering a drug across a host membrane comprising the step of administering the drug within the self assembled structures of the present invention.

In certain embodiments, the present invention provides a filter based on the nanostructures of the present invention.

Nanotube Forming Peptides

Table 2 shows the different oligopeptides synthesized and investigated so far. The hydrophilic moiety of the molecule is given by one or two aspartic acids. Due to the method of synthesis, an additional carboxylic group is linked to the last aspartic acid. Consequently, the head group has potentially three negative charges. The lipophilic tail of the peptides is constituted of six consecutive hydrophobic amino acids. The shape and the global hydrophobicity of the peptide can thus be conveniently fine-tuned by increasing the aliphatic side group of the amino acid. The calculated pI for the investigated peptides gives value from 3.56 to 3.8 depending on the number of aspartic acids constituting the hydrophilic head group. At pH under these values, the peptides are mainly protonated and, thus uncharged. Consequently, their solubilities in water are compromised.

TABLE 2

Synthesized surfactant peptides of the current invention

| Name | Sequence Name N-terminus → C-terminus | Molecular Weight [g/mol] | Calculated pI |
|---|---|---|---|
| (SEQ ID NO: 35) | $A_6D$ [Acetyl]-AAAAAAD-$CO_2$ | 557.6 | 3.80 |
| (SEQ ID NO: 36) | $V_6D$ [Acetyl]-VVVVVVD-$CO_2$ | 725.9 | 3.80 |
| (SEQ ID NO: 37) | $A_6D_2$ [Acetyl]-AAAAAADD-$CO_2$ | 671.7 | 3.56 |
| (SEQ ID NO: 38) | $V_6D_2$ [Acetyl]-VVVVVVDD-$CO_2$ | 840.0 | 3.56 |
| (SEQ ID NO: 39) | $L_6D_2$ [Acetyl]-LLLLLLDD-$CO_2$ | 924.1 | 3.56 |
| (SEQ ID NO: 40) | $K_2I_6$ KKIIIIII-C(O)$NH_2$ | | |
| (SEQ ID NO: 41) | $K_2L_6$ KKLLLLLL-C(O)$NH_2$ | | |
| (SEQ ID NO: 42) | $K_2A_6$ KKAAAAAA-C(O)$NH_2$ | | |
| (SEQ ID NO: 43) | $K_2V_6$ KKVVVVVV-C(O)$NH_2$ | | |

Molecular models of the peptides synthesized are shown in the FIG. 1, where the hydrophobic part of the molecule is composed of alanine, valine, or leucine respectively. By changing the character of the hydrophobic side chains, we can induce a change in the intermolecular forces with which the tails can interact. In the first group surfactant-like polypeptides, the hydrophilic head group is kept unchanged and we only varied the hydrophobicity of side chain while maintaining the same number of amino acids (see FIG. 1). The alanine (A) side chain consists of one carbon whereas the valine (V) side chain has three carbon groups. The leucine (L) side chain has four carbons. VVVVVVD ($V_6D$) (SEQ ID NO: 36) and AAAAAAD ($A_6D$) (SEQ ID NO: 35) were also synthesized in order to investigate the influence of the hydrophilic head group on the self-assembly behavior of this new class of peptides. These two peptides are made of only one aspartic acid as hydrophilic head group and, consequently, carry two negative charges (C-terminal) instead of three for its analogs VVVVVVDD ($V_6D_2$) (SEQ ID NO: 38) or AAAAAADD ($A_6D_2$) (SEQ ID NO: 37). Besides the variation in electrostatic interactions expected for such a modification of the peptide sequence, the cross-sectional area (a) of the polar head group will be smaller, leading to a decrease in the packing parameter P as describe by Israelachvili[21] ($P=v[a]^{-1}$, where v is the molecular volume, l the molecular length and a is the cross-sectional area of the polar head group).

Figure 2:
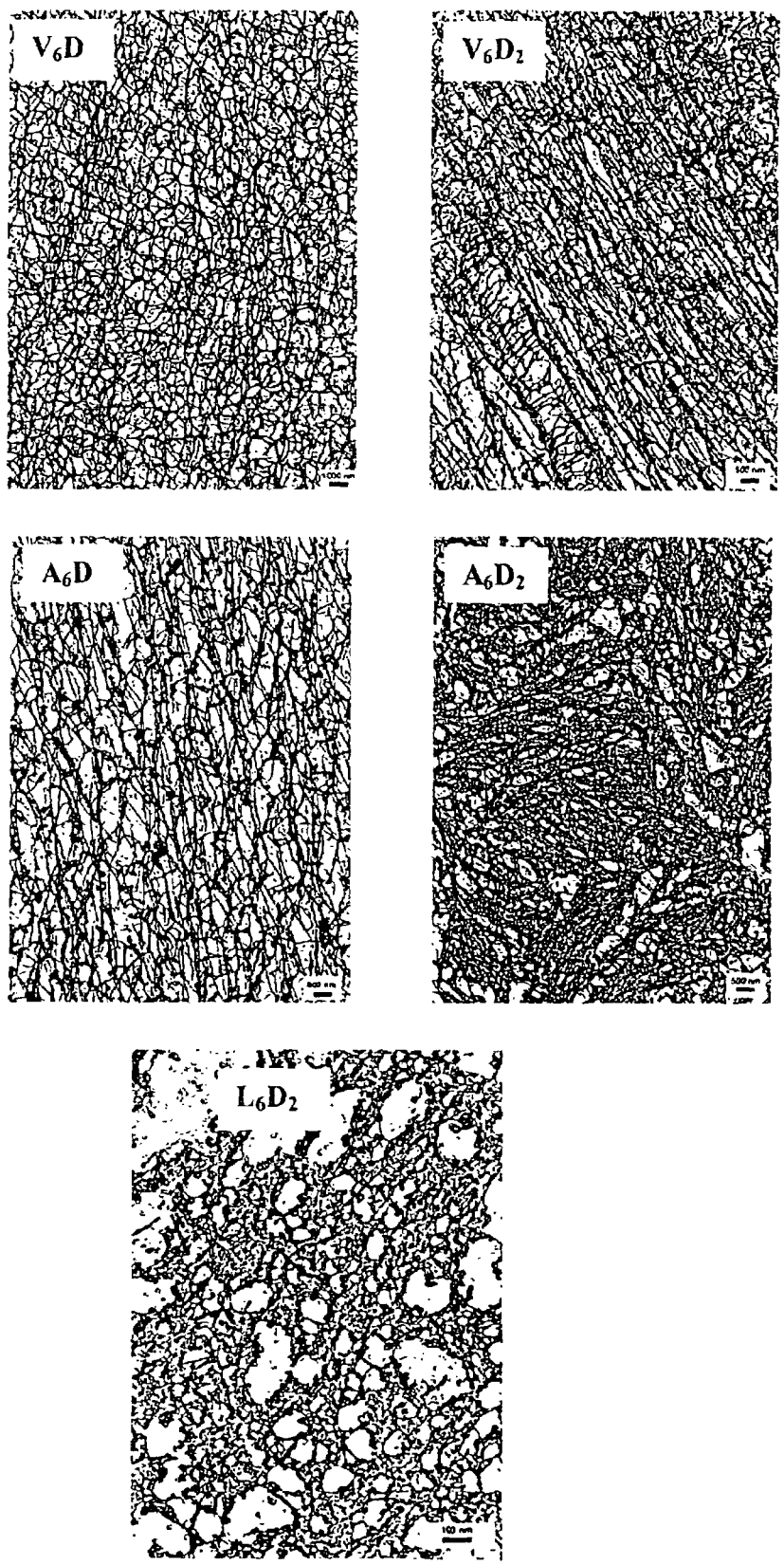
FIG. 2 depicts low resolutions of Cryo-TEM image of surfacant peptides at pH 7. The Peptide concentrations are 5 mg/ml.
Figure 3:
FIG. 3 FIG. 3 depicts low resolution of Cryo-TEM image of the aqueous solution of VVVVVVD ($V_6D$) (SEQ ID NO: 36).

Cryo-transmission electron microscopy experiments were performed on aqueous solution of the different peptides at a concentration of 5 mg/ml. In order to solubilize these peptides in water, it was necessary to deprotonate the carboxylic groups by adjusting the pH with a solution of sodium hydroxide 0.1N. The oligopeptides investigated start to be soluble in water at pH 5 to 6, depending on the amino acid sequence. All the experiments presented in this work were carried out using peptide solutions at pH 7. Cryo-TEM experiments for these systems indicated that the charged oligopeptides exist as a dense network of entangled nanotubes of diameter ranging from 25 nm to 50 nm (FIG. 2). The cylindrical assemblers present a three-dimensional transient network somehow similar to flexible polymers in their semidilute or concentrated solutions[22]. It should be pointed out that, in the electron micrographs, only a two-dimensional projection of the peptides nanotubes could be imaged. The network below and above a defined point in the space could be relatively distant in three dimensions, while appearing superimposed in the two-dimensional projection. This result in a denser appearance of the two-dimensional network. Cryo-TEM micrographs of VVVVVVD ($V_6D$) (SEQ ID NO: 36), VVVVVVDD ($V_6D_2$) (SEQ ID NO: 38) and AAAAAAD ($A_6D$) (SEQ ID NO: 35) exhibit very similar cylindrical morphologies. These self-assemblies have high axial ratios and extend in length to several tens of micrometers. Additionally, one can easily identify many three-fold junctions or branchings connecting the nanotubes and thus forming the final network. It seems that the branches connecting two nanotubes have cylindrical morphologies of smaller diameter (about 25 nm). Alternatively, two nanotubes could fuse together to form a tentative 4-arm branch. It has been shown that this kind of branching is energetically unstable and, thus, those observed in FIG. 3 are most likely due to the 2-D representation of a spatial network.

The possibility that branched supramolecular organizations exist has attracted considerable interest[22-24]. Evidence of branching has mainly been reported for aqueous surfactant solutions but reversed structure such as lecithin organogels can also form three-fold junctions[23]. Branch points produce patches having mean curvature opposite to that of the portion far from the junction[25]. Many reports claimed the importance of branching points to visco-elastic properties of polymer-like systems[22]. Cates et al.[26-27] have provided a statistical description of branches vs. entanglements whereas Lequeux[28] has modeled the expected effects on the Theological properties.

Cryo-TEM micrograph of AAAAAADD ($A_6D_2$) (SEQ ID NO: 37) shows a slightly different pattern with a denser network. In fact, one can easily recognize nanotubes of about 50 nm diameter linked by an increased numbers of three-fold junction. As a result, the branches are more abundant than those observed in the samples VVVVVVD ($V_6D$) (SEQ ID NO: 36), VVVVVVD ($V_6D_2$) (SEQ ID NO: 38) and AAAAAAD ($A_6D$) (SEQ ID NO: 37). They have also a smaller axial ratio and a much smaller average diameter of about 10 to 15 nm. LLLLLLD ($L_6D_2$) (SEQ ID NO: 39) is the most hydrophobic compound with the tail constituted of six leucines. Aqueous solution of LLLLLLDD ($L_6D_2$) (SEQ ID NO: 39) does not exhibit any nanotubular structures but rather a network of entangled rodlike micelles. These molecular assemblies are very similar to threadlike micellar systems made from traditional amphiphilic molecules such as cetyltrimethylammonium bromide (CTAB)[29-30]. It should be noted that a large number of vesicle-like spherical assemblies also appear in the TEM micrograph.

Figure 4:
FIG. 4 depicts Cryo-transmission electron microscopy (Cryo-TEM) images of the AAAAAAD ($A_6D$) (SEQ ID NO: 35) at high resolution.

Cryo-TEM micrograph at high resolution provides a detailed structure of the peptide nanotubes formed by AAAAAAD (SEQ ID NO: 35) (see FIG. 4). The presence of hollow tubular structures is clearly visible under these conditions, giving rise to two spatially separated hydrophilic surfaces. Additionally, helical pitches between 150 and 200 nm, depending on the nanotubes diameter, were also observed. Similar results have been documented with hollow cylinders formed of bilayer membrane of diacetylenic lipids[31]. Theories based on molecular chirality have been developed to explain the presence of helical markings that wind around the cylinders[32].

Figure 5:
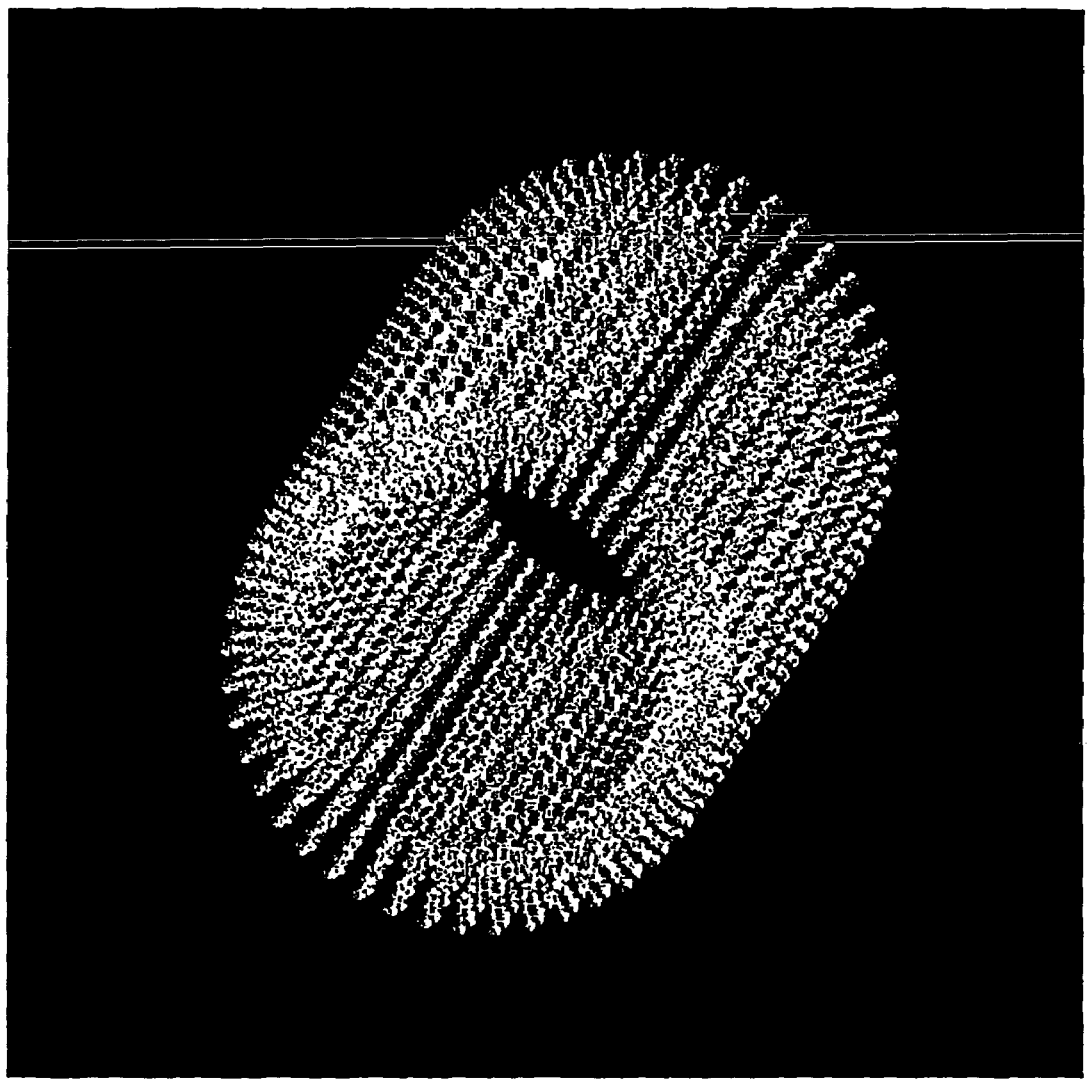
FIG. 5 depicts a structural organization suggested by molecular modeling of the peptide nanotube.

A possible structural organization is suggested by molecular modeling of the peptide nanotubes (FIG. 5). It is proposed that subunits rings are first formed through self-assembly of peptides monomers in bilayer topology, where hydrophilic head groups remain exposed to the continuous media. The cylindrical arrays can subsequently be stacked via non-covalent interactions to form continuous tubes.

Tubular nanostructure made from self-assembly of this new class of polypeptide is only the first system discovered so far. It is anticipated that, very much like surfactant self-assemblies, fine-tuning of the monomer properties will give rise to a wide range of nanostructures, thus opening new innovative avenues for the development of biomaterials. It is envisioned that a number of variables can be examined. For example, increasing the length of the hydrophobic chain may introduce more rigidity in the membranes and perhaps lead to tubes of greater diameter with smaller curvature. In the same way changing the character of the hydrophobic side chains would be important. Using phenol alanine, for example, will certainly change the fluidity of the hydrophobic phase and is likely to change the morphology and the dimensions of the network.

Experiments can also be carried out in which variations in the charged residue can be explored. We have already shown in a preliminary fashion that putting two charged residues into the aqueous phase results in building a similar structure. However, addition of a third charged residue de-stabilizes it, probably by making the individual molecule soluble in water, thereby preventing the self-association into membranes. Thus, one of the elements to be explored systematically is the relative balance of the hydrophobic chain, versus the hydrophilic ends. It is possible that the use of longer hydrophobic segments could stabilize the membrane so that we could introduce many more variations in the hydrophilic end. The kind of experiments that could be carried out might involve the use of a mixture of positively charged and negatively charged residues in the hydrophilic end with the same hydrophobic tail. This might lead to development of a different organization of the tubes. By changing the ratio of positive to negative, it is likely that we will be able to control some elements of the self-assembly and therefore control the morphology of the nanotubes.

Work on this novel assembly mode is just underway, and one of our first goals is to obtain more physical evidence about the nature of the aggregation. In this regard, solution X-ray diffraction photographs will be useful in understanding elements of the packing. By substituting bromine or iodine atoms in the hydrophilic end, we could then determine the distance between these heavy atoms in the X-ray scattering diagram and in this way draw inferences about the nature of the assembly. A systematic series of studies of this type in which the hydrophobic tail is elongated would provide the necessary information about the organization of these nanotubes.

Through the use of longer and possibly less flexible hydrophobic chains, it may be possible to begin to build structures on the hydrophilic surface of the nanotube by extending the peptide chain, for example, to make small α-helical segments. Research of this type could lead to the development of nanotubes with textured surfaces, that is, surfaces in which a series of different structural motifs could be investigated. For example, helices or even β-sheet structures could be assembled on the outside of the membrane. The driving force in forming the membrane is the hydrophobicity of the hydrophobic peptide. One of the elements that would be of interest to explore is the use of block co-polymers in the hydrophobic phase. For example, imagine a system made with the general formula $f_n a_m$ that has a hydrophobic tail in which n-phenol alanines are linked to m-alanines. This hydrophobic tail would have a rather large anchor of phenol alanine rings at one end. The use of a structured hydrophobic anchor of this type would make it possible to explore the effects of having these residues assembled in opposite orientation with the hydrophobic residues at either end. In this way one might in effect "lock" the hydrophobic domains together by having bulky phenol alanine residues at one end and less bulky or slimmer alanine residues at the other end. This should have a significant effect in producing a membrane that is more rigid and perhaps capable of forming very large tubes with a considerably greater radius of curvature.

At this stage the inventors realize that a variety of different nanosheets and nanotubes can be engineered through the use of the great deal of chemical variation found in the 20 different amino acids.

Peptide Di- and Tri-Block Co-Polymers

Block co-polymers using organic compounds have emerged as a very well developed system to construct new materials that have a broad range of applications. This system can be readily extended to biological building materials. There are 20 natural L-amino acids, their mirror image of D-amino acids and a variety of non-natural amino acids, all of which can be readily used as the building blocks to construct the bio-based block co-polymers.

There are a number of advantages to build these biological block co-polymers using the well-developed synthetic chemistry: 1) these block co-polymers are amenable for molecular systematic design, modification, and synthesis; 2) these designed block co-polymers can be subjected to extensive molecular modeling and simulations before synthesis; 3) these block co-polymers can be highly purified to be mono-dispersed materials; 4) a combinatorial approach can be employed to systematically characterize these co-polymers at various ratios; 5) instrumentation that has been used for polymer research can be readily used to characterize the biological block co-polymer; 6) these nanobuilding blocks can be used to construct a number of unexpected and interesting materials; and 7) the peptides can also be synthesized in vitro or in vivo.

Many block copolymer-like motifs have been found in proteins. Some of which are important for the protein biological function and others have been used as a tool for discovery of new proteins in cells. Research in this underexplored area will likely produce some unexpected findings that can not only provide us with new knowledge of complexity in polymer science but may also provide insight into protein-protein interactions and protein folding. These bio-based block co-polymers may be developed for a variety of applications. Since the combinations are extremely large, formulas 1-10 describe the generic block copolymer sequences and two tables listing the peptide block copolymers are presented in Tables 3 and 4.

| Sequence (N → C) | Formula |
|---|---|
| $(\phi)_m(+)_n$ | 1 |
| $(+)_n(\phi)_m$ | 2 |
| $(\phi)_m(-)_n$ | 3 |
| $(-)_n(\phi)_m$ | 4 |
| $(-)_n(\phi)_m(-)_n$ | 5 |
| $(+)_n(\phi)_m(+)_n$ | 6 |
| $(\phi)_m(-)_n(\phi)_m$ | 7 |
| $(\phi)_m(+)_n(\phi)_m$ | 8 |
| $(+)_n(\phi)_m(-)_n$ | 9 |
| $(-)_n(\phi)_m(+)_n$ | 10 |

Where (+), (−), (φ), m, and n are defined as before.

TABLE 3

Synthesized Di-Block Co-Polymers.

| Name | No. of residues | Sequence (N→C) |
|---|---|---|
| DA20 (SEQ ID NO: 44) | 20 | DDDDDDDDDDAAAAAAAAAA |
| AD20 (SEQ ID NO: 45) | 20 | AAAAAAAAAADDDDDDDDDD |
| AE20 (SEQ ID NO: 46) | 20 | EEEEEEEEEEAAAAAAAAAA |
| EA20 (SEQ ID NO: 47) | 20 | AAAAAAAAAAEEEEEEEEEE |
| DV20 (SEQ ID NO: 48) | 20 | DDDDDDDDDDVVVVVVVVVV |

TABLE 3-continued

Synthesized Di-Block Co-Polymers.

| Name | No. of residues | Sequence (N→C) |
|---|---|---|
| VD20 (SEQ ID NO: 49) | 20 | VVVVVVVVVVDDDDDDDDDD |
| DP20 (SEQ ID NO: 50) | 20 | DDDDDDDDDDPPPPPPPPPP |
| PD20 (SEQ ID NO: 51) | 20 | PPPPPPPPPPDDDDDDDDDD |
| HA20 (SEQ ID NO: 52) | 20 | AAAAAAAAAAHHHHHHHHHH |
| AH20 (SEQ ID NO: 53) | 20 | HHHHHHHHHHAAAAAAAAAA |
| KA20 (SEQ ID NO: 54) | 20 | KKKKKKKKKKAAAAAAAAAA |
| AK20 (SEQ ID NO: 55) | 20 | AAAAAAAAAAKKKKKKKKKK |
| RA20 (SEQ ID NO: 56) | 20 | RRRRRRRRRRAAAAAAAAAA |
| AR20 (SEQ ID NO: 57) | 20 | AAAAAAAAAARRRRRRRRRR |

D is aspartic acid; A is alanine; E is glutamic acid; V is valine; P is proline; H is histidine; K is lysine; and R is arginine.

TABLE 4

Synthesized Tri-Block Co-Polymers.

| Name | No. of residues | Sequence (N→C) |
|---|---|---|
| DAD30 (SEQ ID NO: 58) | 30 | DDDDDDDDDDAAAAAAAAAADDDDDDDDDD |
| ADA30 (SEQ ID NO: 59) | 30 | AAAAAAAAAADDDDDDDDDDAAAAAAAAAA |
| AEA30 (SEQ ID NO: 60) | 30 | EEEEEEEEEEAAAAAAAAAAEEEEEEEEEE |
| EAE30 (SEQ ID NO: 61) | 30 | AAAAAAAAAAEEEEEEEEEEAAAAAAAAAA |
| DVD30 (SEQ ID NO: 62) | 30 | DDDDDDDDDDVVVVVVVVVVDDDDDDDDDD |
| VDV30 (SEQ ID NO: 63) | 30 | VVVVVVVVVVDDDDDDDDDDVVVVVVVVVV |
| DP30 (SEQ ID NO: 64) | 30 | DDDDDDDDDDPPPPPPPPPPDDDDDDDDDD |
| PDP30 (SEQ ID NO: 65) | 30 | PPPPPPPPPPDDDDDDDDDDPPPPPPPPPP |
| HAH30 (SEQ ID NO: 66) | 30 | AAAAAAAAAAHHHHHHHHHHAAAAAAAAAA |
| AHA30 (SEQ ID NO: 67) | 30 | HHHHHHHHHHAAAAAAAAAAHHHHHHHHHH |
| KAK30 (SEQ ID NO: 68) | 30 | KKKKKKKKKKAAAAAAAAAAKKKKKKKKKK |
| AKA30 (SEQ ID NO: 69) | 30 | AAAAAAAAAAKKKKKKKKKKAAAAAAAAAA |
| RAR30 (SEQ ID NO: 70) | 30 | RRRRRRRRRRAAAAAAAAAARRRRRRRRRR |
| ARA30 (SEQ ID NO: 71) | 30 | AAAAAAAAAARRRRRRRRRRAAAAAAAAAA |
| KAD30 (SEQ ID NO: 72) | 30 | KKKKKKKKKKAAAAAAAAAADDDDDDDDDD |
| KAE30 (SEQ ID NO: 73) | 30 | KKKKKKKKKKAAAAAAAAAAEEEEEEEEEE |
| RVD30 (SEQ ID NO: 74) | 30 | RRRRRRRRRRVVVVVVVVVVDDDDDDDDDD |
| KPD30 (SEQ ID NO: 75) | 30 | KKKKKKKKKKPPPPPPPPPPDDDDDDDDDD |

TABLE 4-continued

Synthesized Tri-Block Co-Polymers.

| Name | No. of residues | Sequence (N→C) |
|---|---|---|
| | | ++++++++++     ---------- |
| HAE30 (SEQ ID NO: 58) | 30 | HHHHHHHHHHAAAAAAAAAAEEEEEEEEEE |

D is aspartic acid; A is alanine; E is glutamic acid; V is valine; P is proline; H is histidine; K is lysine; and R is arginine.

Forming Gold Nanostructures

The ability of sulfur to form covalent bonds with gold surfaces is well documented in the art[1]. The interaction between gold and such sulfur-containing functional groups is a well-studied science, and a nonlimiting representative exemplary list of such sulfur-containing functionalities may be found in an article entitled "Wet Chemical Approaches to the Characterization of Organic Surfaces: Self-Assembled Monolayers, Wetting and the Physical-Organic Chemistry of the Solid-Liquid Interface" by G. W. Whitesides and Paul E. Laibinis, Langmuir, 6, 87 (1990), incorporated herein by reference. Some general concepts can be garnered from the literature and include the following. Any functional group terminated with a sulfur (R-S) can be assembled on gold; sulfur coordinates strongly to gold which allows monolayer formation in the presence of many other functional groups; gold is resistant to oxidation, which often inhibits monolayer assembly on other materials; and monolayers pack densely on gold.

The current invention is particularly well suited to exploit this chemistry. Particularly preferred in the present invention is a gold surface, and a thiol. Modification of the nanotube walls can be carried out by selectively choosing amino acids of different properties. Substitution of one of the amino acids listed in any of the previous compounds with the amino acid cysteine with its thiol -SH functionality gives the potential of both anchoring the nanotubes upon a gold surface and incorporating a gold coating upon the nanotubes. The gold coating can be applied via electroplating gold in the presence of cysteine including nanotubes. Importantly, the gold-bearing peptides may constitute only a portion of the peptides making up a given nanotube.

One novel application of this technology would be to use radio frequency energy to open a gold-bearing nanotube, thereby releasing its contents. For example, this approach may be utilized on gold-bearing nanotubes that contain a drug, thereby releasing the drug within an organism that has ingested or been injected with the aforementioned gold-bearing nanotube.

Another novel application would be in the field of molecular wires, where gold particles can be organized by the peptide nanotubes into a wire, and the wires can be fabricated into a circuit.

Filtration Systems Based on Nanotubes

Filtration systems based on both size and charge lend themselves very well to the current invention. The oligopeptide nanotubes of the current invention form with regular diameters on the order of 50 nm. However, as with surfactants, increasing the length of the hydrophobic tail may lead to a more rigid nanotube and larger tubular diameter. Separation of macromolecules from small molecules is the basis of dialysis and it is envisioned by the inventors that the current invention will lead to tailor made filtration systems for separating molecules based on size. Additionally, the charge of the internal core is adjustable by selectively choosing the amino acids that make up the head portion of the oligopeptide. This would allow filtration based not on size but on charge. For instance, a nanotube with a predominantly anionic head would allow cations to pass but repel anions. Likewise, a nanotube with a predominantly cationic head would allow anions to pass but not cations.

Delivery of Guest/Drug Compounds

The nanotubes of the present invention can be carriers for bilogically active materials. Temporary preservation of functional properties of a carried species, as well as controlled release of the species into local tissues or systemic circulation, are possible. Proper choice of amino acids can produce nanotubes with a range of permeability and diameter sizes suitable for a variety of applications in medical treatments. In an analogous manner to cationic liposomes, positively charged compound of the present invention can be used to deliver genes via plasmids. Conversely, negatively charged compounds of the invention can be used to deliver positively charged guests. The current invention is superior to liposome delivery systems in that the nanotubes fuse with the lipid bilayers and do not deform the cell as do liposomes.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage formns which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrer" as used herein means a pharmnaceutically-acceptable material, composition or vehicle, such as a liquid or solid filler, diluent, excipient, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include:

(1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharnaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pahmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a phannaceutically-acceptable metal cation, with amrnonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and-lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosagc forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quatemary. ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermnal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the, age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject co,pounds, as described above, formulated together with one or more pharmaceutically acceptable carriers (additives) and/ or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Oreg., U.S.A., 1977).

Incorporation By Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

REFERENCES

1. Whitesides, G. M.; Mathias, J. P. and Seto, C. T. *Science* 1991, 254, 1312-1319.
2. Langer, R. S.; Vacanti, J. P. *Science* 1993, 260, 920.
3. Hubbell, J. A. *MRS Bulletin* 1996, 21(11), 33.
4. Zhang, S.; Lockshin, C.; Cook, R.; Rich, A. *Biopolymers* 1994, 34, 663.
5. Aggeli, A., Bell, M., Boden, N., Keen, J. N., Knowles, P. F., McLeish, T.C., Pitkeathly, M. and Radford, S. E. *Nature* 1997, 386, 259-262.
6. Ghadiri, M. R., Granja, J. R., Buehler, L. K. *Nature* 1994, 369, 301-304.
7. Bieri, C., Ernst, O. P., Heyse, S., Hofmann, K. P. and Vogel, H. *Nat Biotechnol* 1999, 17, 1105-1108.
8. O'Shea, E. K., Rutkowski, R. and Kim, P. S. *Science* 1989, 243, 538-542.
9. Hecht, M. H., Richardson, J. S. and Richardson, D. C. *Science* 1990, 249, 884-891.
10. Baker, D. and DeGrado, W. F. *Curr Opin Struct Biol* 1999, 9, 485-486.
11. Zhang, S., Holmes, T. C., DiPersio, C. M., Hynes, R, O., Su, X. and Rich, A. *Biomaterials* 1995,16, 1385-1393.
12. Zhang, S., Holmes, T., Lockshin, C. and Rich, A. *Proc Natl Acad Sci USA* 1993, 90, 3334-3338.
13. Leon, E. J., Verma, N., Zhang, S., Lauffenburger, D. A. and Kamm, R. D. *J. Biomaterials Science: Polymer Edition* 1998, 9, 293-312.
14. Zhang, S. and Rich, A. *Proc Natl Acad Sci USA* 1997, 94, 23-28.
15. Hol, W. G., Halie, L. M. and Sander, C. *Nature* 1981, 294, 532-536.
16. Minor, D. L. Jr, and Kim, P. S. *Nature* 1996, 380, 730-734.
17. Tan, S. and Richmond, T. J. *Nature* 1998, 391, 660-666.
18. Takahashi, Y., Ueno, A. and Mihara, H. *Bioorg Med Chem* 1999, 7, 177-185.
19. Zhang, S., Yan, L., Altman, M., Lassie, M., Nugent, H., Frankel, F., Lauffenburger, D. A., Whitesides, G. M. and Rich, A. *Biomaterials* 1999, 20, 1213-1220.
20. Bong, D. T.; Clark, T. D.; Granja, J. R.; Ghadiri, M. R. *Angew. Chem. Int. Ed.* 2001, 40, 988.
21. Israelachvili, J. N.; Mitchell, D. J.; Ninham, B. W. *J Chem. Soc. Faraday Trans. II* 1976, 72, 1525.
22. Magid, J. L. *J. Phys. Chem. B* 1998, 102,4064.
23. Shchipunov, Y. A.; Hoffmann, H. langmuir 1998, 14, 6350.
24. Drye, T. J.; Cates, M. E. J. *J. Chem. Phys.* 1993, 98, 9790.
25. Shikata, T.; Imai, S. Langmuir 2000,16,4840.
26. Cates, M. E. *Macromol.* 1987, 20, 2289.
27. Cates, M. E. *J. Phys.* 1988, 49, 1593.
28. Lequeux, F. *Curr. Opinion Colloid Interface Sci.* 1996, 1, 337.
29. Nemoto, N.; Kuwahara, M.; Yao, M. L.; Osaki, K. *Langmuir* 1995, 11, 30.
30. Hassan, P. A.; Yakhmi, J. V. *Langrnuir* 2000, 16, 7187.
31. Schnur, J. M. *Science* 1993, 262, 1669.
32. Selinger, J. V.; MacKintosh, F. C.; Schnur, J. M. *Phys Rev. E* 1996, 53, 3804.

We claim:

1. A method of forming a self-assembled nanostructure comprising forming an aqueous mixture of peptides having a formula selected from the group consisting of:

$(\Phi)_m(+)_n$      1 (N→C);

$(+)_n(\Phi)_m$      2 (N→C);

$(\Phi)_m(-)_n$      3 (N→C);

$(-)_n(\Phi)_m$      4 (N→C);

$(-)_n(\Phi)_m(-)_n$      5 (N→C);

$(+)_n(\Phi)_m(+)_n$      6 (N→C);

$(\Phi)_m(-)_n(\Phi)_m$      7 (N→C);

$(\Phi)_m(+)_n(\Phi)_m$      8 (N→C);

$(+)_n(\Phi)_m(-)_n$      9 (N→C);

and $(-)_n(\Phi)_m(+)_n$      10 (N→C)

wherein:

($\Phi$) represents independently for each occurrence a natural or non-natural amino acid comprising a hydrophobic sidechain;

(+) represents independently for each occurrence a natural or non-natural amino acid comprising a sidechain that is cationic at physiological pH;

(−) represents independently for each occurrence a natural or non-natural amino acid comprising a sidechain that is anionic at physiological pH;

wherein the terminal amino acids are optionally substituted;

m for each occurrence represents an integer greater than or equal to 5; and n for each occurrence represents an integer greater than or equal to 1;

under conditions suitable for self-assembly of the peptides into a nanostructure and allowing the nanostructure to be formed.

2. The method of claim 1, wherein the peptides have the formula:

$(\Phi)_m(+)_n$      1 (N→C);

($\Phi$) represents independently for each occurrence a natural or non-natural amino acid comprising a hydrophobic sidechain and wherein the N terminal amino acid is substituted; and (+) represents independently for each occurrence a natural or non-natural amino acid comprising a sidechain that is cationic at physiological pH and wherein the C terminal amino acid is substituted.

3. The method of claim 1, wherein the peptides have the formula:

$(+)_n(\Phi)_m$      2 (N→C)

($\Phi$) represents independently for each occurrence a natural or non-natural amino acid comprising a hydrophobic sidechain wherein the C terminal amino acid is substituted; and (+) represents independently for each occurrence a natural or non-natural amino acid comprising a sidechain that is cationic at physiological pH and wherein the N terminal amino acid is unsubstituted.

4. The method of claim 1, wherein the peptides have the formula:

$(\Phi)_m(-)_n$      3 (N→C)

($\Phi$) represents independently for each occurrence a natural or non-natural amino acid comprising a hydrophobic sidechain wherein the N terminal amino acid is substituted; and (−) represents independently for each occurrence a natural or non-natural amino acid comprising a sidechain that is anionic at physiological pH wherein the C terminal amino acid is unsubstituted.

5. The method of claim 1, wherein the peptides have the formula:

$(-)_n(\Phi)_m$      4 (N→C)

($\Phi$) represents independently for each occurrence a natural or non-natural amino acid comprising a hydrophobic sidechain wherein the C terminal amino acid is substituted; and (−) represents independently for each occurrence a natural or non-natural amino acid comprising a sidechain that is anionic at physiological pH wherein the N terminal amino acid is substituted.

6. The method of claim 1 wherein the peptides have the formula:

$(-)_n(\Phi)_m(-)_n$      5 (N→C)

(−) represents independently for each occurrence a natural or non-natural amino acid comprising a sidechain that is anionic at physiological pH wherein the C terminal amino acid is unsubstituted and the N terminal amino acid is substituted.

7. The method of claim 1, wherein the peptides have the formula:

$(+)_n(\Phi)_m(+)_n$      6 (N→C)

(+) represents independently for each occurrence a natural or non-natural amino acid comprising a sidechain that is cationic at physiological pH wherein the C terminal amino acid is substituted and the N terminal amino acid is unsubstituted.

8. The method of claim 1, wherein the peptides have the formula:

$$(\Phi)_m(-)_n(\Phi)_m \quad 7\ (N\rightarrow C)$$

($\Phi$) represents independently for each occurrence a natural or non-natural amino acid comprising a hydrophobic sidechain wherein the N and C terminal amino acids are substituted.

9. The method of claim 1, wherein the peptides have the formula:

$$(\Phi)_m(+)_n(\Phi)_m \quad 8\ (N\rightarrow C)$$

($\Phi$) represents independently for each occurrence a natural or non-natural amino acid comprising a hydrophobic sidechain wherein the N and C terminal amino acids are substituted.

10. The method of claim 1, wherein the peptides have the formula:

$$(+)_n(\Phi)_m(-)_n \quad 9\ (N\rightarrow C)$$

(−) represents independently for each occurrence a natural or non-natural amino acid comprising a sidechain that is anionic at physiological pH wherein the C terminal amino acid is unsubstituted; and (+) represents independently for each occurrence a natural or non-natural amino acid comprising a sidechain that is cationic at physiological pH and wherein the N terminal amino acid is unsubstituted.

11. The method of claim 1, wherein the peptides have the formula:

$$(-)_n(\Phi)_m(+)_n \quad 10\ (N\rightarrow C)$$

(−) represents independently for each occurrence a natural or non-natural amino acid comprising a sidechain that is anionic at physiological pH wherein the N terminal amino acid is substituted; and (+) represents independently for each occurrence a natural or non-natural amino acid comprising a sidechain that is cationic at physiological pH wherein the C terminal amino acid is substituted.

12. The method of claim 1, wherein the peptides have the formula 1, 3, 4, 5, 7, 8, or 10 and the N terminal amino acid is substituted by an acetyl group.

13. The method of claim 1, wherein the peptides have the formula 1, 2, 4, 6, 7, 8, or 10 and the C terminal amino acid is substituted by an amino group.

14. The method of claim 1, wherein n is 1.

15. The method of claim 14, wherein m is 5, 6 or 7.

16. The method of claim 15, wherein ($\Phi$) in each instance is alanine, valine, leucine, isoleucine or proline.

17. The method of claim 15, wherein (−) in each instance is aspartic acid or glutamic acid.

18. The method of claim 15, wherein (+) in each instance is histidine, lysine or arginine.

19. The method of claim 1, wherein the peptides are selected from the group consisting of AAAAAAD (SEQ ID NO. 35), VVVVVVD (SEQ ID NO. 36), AAAAAADD (SEQ ID NO. 37), VVVVVVDD (SEQ ID NO. 38), and LLLLLLDD (SEQ ID NO. 39) wherein the N terminal amino acid is substituted with an acetyl group.

20. The method of claim 1, wherein the peptides are selected from the group consisting of KKIIIIII (SEQ ID NO. 40), KKLLLLLL (SEQ ID NO. 70), KKAAAAAA (SEQ ID NO. 42), KKVVVVVV (SEQ ID NO. 43) wherein the C terminal amino acid is substituted with an amino group.

21. The method of claim 1, wherein the peptide is a diblock or triblock copolymer wherein n is an integer greater than or equal to 5.

22. The method of claim 21, wherein n and m are independently selected from the integers 5, 6, 7, 8, 9 or 10.

23. The method of claim 22, wherein ($\Phi$) in each instance is alanine, valine, leucine or proline.

24. The method of claim 22, wherein (−) in each instance is aspartic acid or glutamic acid.

25. The method of claim 22, wherein (+) in each instance is histidine, lysine or arginine.

26. The method of claim 1, wherein the peptides have the sequence
DDDDDDDDDDAAAAAAAAAA (SEQ ID NO. 44),
AAAAAAAAAADDDDDDDDDD (SEQ ID NO. 45),
EEEEEEEEEEAAAAAAAAAA (SEQ ID NO. 46),
AAAAAAAAAAEEEEEEEEEE (SEQ ID NO. 47),
DDDDDDDDDDVVVVVVVVVV (SEQ ID NO. 48),
VVVVVVVVVVDDDDDDDDDD (SEQ ID NO. 49),
DDDDDDDDDDPPPPPPPPPP (SEQ ID NO. 50),
PPPPPPPPPPDDDDDDDDDD (SEQ ID NO. 51),
AAAAAAAAAAHHHHHHHHHH (SEQ ID NO. 52),
HHHHHHHHHHAAAAAAAAAA (SEQ ID NO. 53),
KKKKKKKKKKAAAAAAAAAA (SEQ ID NO. 54),
AAAAAAAAAAKKKKKKKKKK (SEQ ID NO. 55),
RRRRRRRRRRAAAAAAAAAA (SEQ ID NO. 56), or
AAAAAAAAAARRRRRRRRRR (SEQ ID NO. 57).

27. The method according to claim 21, wherein the peptides have the formula:
DDDDDDDDDDAAAAAAAAAADDDDDDDDDD (SEQ ID NO. 58),
EEEEEEEEEEAAAAAAAAAAEEEEEEEEEE (SEQ ID NO. 60),
DDDDDDDDDDVVVVVVVVVVDDDDDDDDDD (SEQ ID NO. 62),
DDDDDDDDDDPPPPPPPPPPDDDDDDDDDD (SEQ ID NO. 64),
HHHHHHHHHHAAAAAAAAAAHHHHHHHHHH (SEQ ID NO. 67),
KKKKKKKKKKAAAAAAAAAAKKKKKKKKKK (SEQ ID NO. 68),
RRRRRRRRRRAAAAAAAAAARRRRRRRRRR (SEQ ID NO. 70),
AAAAAAAAAADDDDDDDDDDAAAAAAAAAA (SEQ ID NO. 59),
AAAAAAAAAAEEEEEEEEEEAAAAAAAAAA (SEQ ID NO. 61),
VVVVVVVVVVDDDDDDDDDDVVVVVVVVVV (SEQ ID NO. 63),
PPPPPPPPPPDDDDDDDDDDPPPPPPPPPP (SEQ ID NO. 65),
AAAAAAAAAAHHHHHHHHHHAAAAAAAAAA (SEQ ID NO. 66),
AAAAAAAAAAKKKKKKKKKKAAAAAAAAAA (SEQ ID NO. 69),
AAAAAAAAAARRRRRRRRRRAAAAAAAAAA (SEQ ID NO. 71),
KKKKKKKKKKAAAAAAAAAADDDDDDDDDD (SEQ ID NO. 72),
KKKKKKKKKKAAAAAAAAAAEEEEEEEEEE (SEQ ID NO. 73),
RRRRRRRRRRVVVVVVVVVVDDDDDDDDDD (SEQ ID NO. 74),
KKKKKKKKKKPPPPPPPPPPDDDDDDDDDD (SEQ ID NO. 75), and
HHHHHHHHHHAAAAAAAAAAEEEEEEEEEE (SEQ ID NO. 76).

28. The method of claim 1, wherein the nanostructure is a nanotube.

29. The method of claim 1, wherein the nanostructure is a micelle.

30. A self-assembled nanostructure comprising forming an aqueous mixture of peptides having a formula selected from the group consisting of:

$(\Phi)_m(+)_n$      1 (N→C);

$(+)_n(\Phi)_m$      2 (N→C);

$(\Phi)_m(-)_n$      3 (N→C);

$(-)_n(\Phi)_m$      4 (N→C);

$(-)_n(\Phi)_m(-)_n$      5 (N→C);

$(+)_n(\Phi)_m(+)_n$      6 (N→C);

$(\Phi)_m(-)_n(\Phi)_m$      7 (N→C);

$(\Phi)_m(+)_n(\Phi)_m$      8 (N→C);

$(+)_n(\Phi)_m(-)_n$      9 (N→C);

and $(-)_n(\Phi)_m(+)_n$      10 (N→C)

wherein:
- ($\Phi$) represents independently for each occurrence a natural or non-natural amino acid comprising a hydrophobic sidechain;
- (+) represents independently for each occurrence a natural or non-natural amino acid comprising a sidechain that is cationic at physiological pH;
- (−) represents independently for each occurrence a natural or non-natural amino acid comprising a sidechain that is anionic at physiological pH;
- wherein the terminal amino acids are optionally substituted;
- m for each occurrence represents an integer greater than or equal to 5; and
- n for each occurrence represents an integer greater than or equal to 1;
- under conditions suitable for self-assembly of the peptides into a nanostructure and allowing the nanostructure to be formed.

31. The nanostructure of claim 30, wherein the peptides have the formula:

$(\Phi)_m(+)_n$      (N→C);

($\Phi$) represents independently for each occurrence a natural or non-natural amino acid comprising a hydrophobic sidechain and wherein the N terminal amino acid is substituted; and (+) represents independently for each occurrence a natural or non-natural amino acid comprising a sidechain that is cationic at physiological pH and wherein the C terminal amino acid is substituted.

32. The nanostructure of claim 30, wherein the peptides have the formula:

$(+)_n(\Phi)_m$      2 (N→C)

($\Phi$) represents independently for each occurrence a natural or non-natural amino acid comprising a hydrophobic sidechain wherein the C terminal amino acid is substituted; and (+) represents independently for each occurrence a natural or non-natural amino acid comprising a sidechain that is cationic at physiological pH and wherein the N terminal amino acid is unsubstituted.

33. The nanostructure of claim 30, wherein the peptides have the formula:

$(\Phi)_m(-)_n$      3 (N→C)

($\Phi$) represents independently for each occurrence a natural or non-natural amino acid comprising a hydrophobic sidechain wherein the N terminal amino acid is substituted; and (−) represents independently for each occurrence a natural or non-natural amino acid comprising a sidechain that is anionic at physiological pH wherein the C terminal amino acid is unsubstituted.

34. The nanostructure of claim 30, wherein the peptides have the formula:

$(-)_n(\Phi)_m$      4 (N→C)

($\Phi$) represents independently for each occurrence a natural or non-natural amino acid comprising a hydrophobic sidechain wherein the C terminal amino acid is substituted; and (−) represents independently for each occurrence a natural or non-natural amino acid comprising a sidechain that is anionic at physiological pH wherein the N terminal amino acid is substituted.

35. The nanostructure of claim 30, wherein the peptides have the formula:

$(-)_n(\Phi)_m(-)_n$      5 (N→C)

(−) represents independently for each occurrence a natural or non-natural amino acid comprising a sidechain that is anionic at physiological pH wherein the C terminal amino acid is unsubstituted and the N terminal amino acid is substituted.

36. The nanostructure of claim 30, wherein the peptides have the formula:

$(+)_n(\Phi)_m(+)_n$      6 (N→C)

(+) represents independently for each occurrence a natural or non-natural amino acid comprising a sidechain that is cationic at physiological pH wherein the C terminal amino acid is substituted and the N terminal amino acid is unsubstituted.

37. The nanostructure of claim 30, wherein the peptides have the formula:

$(\Phi)_m(-)_n(\Phi)_m$      7 (N→C)

($\Phi$) represents independently for each occurrence a natural or non-natural amino acid comprising a hydrophobic sidechain wherein the N and C terminal amino acids are substituted.

38. The nanostructure of claim 30, wherein the peptides have the formula:

$(\Phi)_m(+)_n(\Phi)_m$      8 (N→C)

($\Phi$) represents independently for each occurrence a natural or non-natural amino acid comprising a hydrophobic sidechain wherein the N and C terminal amino acids are substituted.

39. The nanostructure of claim 30, wherein the peptides have the formula:

$(+)_n(\Phi)_m(-)_n$      9 (N→C)

(−) represents independently for each occurrence a natural or non-natural amino acid comprising a sidechain that is anionic at physiological pH wherein the C terminal amino acid is unsubstituted; and (+) represents independently for each occurrence a natural or non-natural amino acid comprising a sidechain that is cationic at physiological pH and wherein the N terminal amino acid is unsubstituted.

40. The nanostructure of claim 30, wherein the peptides have the formula:

$$(-)_n(\Phi)_m(+)_n \qquad 10\ (N \to C)$$

(−) represents independently for each occurrence a natural or non-natural amino acid comprising a sidechain that is anionic at physiological pH wherein the N terminal amino acid is substituted; and (+) represents independently for each occurrence a natural or non-natural amino acid comprising a sidechain that is cationic at physiological pH wherein the C terminal amino acid is substituted.

41. The nanostructure of claim 30, wherein the peptides have the formula 1, 3, 4, 5, 7, 8, or 10 and the N terminal amino acid is substituted by an acetyl group.

42. The nanostructure of claim 30, wherein the peptides have the formula 1, 2, 4, 6, 7, 8, or 10 and the C terminal amino acid is substituted by an amino group.

43. The nanostructure of claim 30, wherein n is 1.

44. The nanostructure of claim 43, wherein m is 5, 6 or 7.

45. The nanostructure of claim 30, wherein the peptide is a diblock or triblock copolymer wherein n is an integer greater than or equal to 5.

46. The nanostructure of claim 30, wherein n and m are independently selected from the integers 5, 6, 7, 8, 9 or 10.

47. The nanostructure of claim 30, wherein the nanostructure is a nanotube.

48. The nanostructure of claim 30, wherein the nanostructure is a micelle.

* * * * *

SEQUENCE LISTING

<160> NUMBER OF SEQ ID NOS: 76

<210> SEQ ID NO 1
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 1

Arg Ala Asp Ala Arg Ala Asp Ala Arg Ala Asp Ala Arg Ala Asp Ala

-continued

```
1               5                  10                 15
```

<210> SEQ ID NO 2
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 2

```
Arg Ala Asp Ala Arg Gly Asp Ala Arg Ala Asp Ala Arg Gly Asp Ala
1               5                  10                 15
```

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 3

```
Arg Ala Asp Ala Arg Ala Asp Ala
1               5
```

<210> SEQ ID NO 4
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 4

```
Arg Ala Arg Ala Asp Ala Asp Ala Arg Ala Arg Ala Asp Ala Asp Ala
1               5                  10                 15
```

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 5

```
Arg Ala Arg Ala Asp Ala Asp Ala
1               5
```

<210> SEQ ID NO 6
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 6

```
Ala Glu Ala Lys Ala Glu Ala Lys Ala Glu Ala Lys Ala Glu Ala Lys
1               5                  10                 15
```

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 7

```
Ala Glu Ala Lys Ala Glu Ala Lys
1               5
```

<210> SEQ ID NO 8
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 8

Arg Ala Glu Ala Arg Ala Glu Ala Arg Ala Glu Ala Arg Ala Glu Ala
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 9

Arg Ala Glu Ala Arg Ala Glu Ala
1               5

<210> SEQ ID NO 10
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 10

Lys Ala Asp Ala Lys Ala Asp Ala Lys Ala Asp Ala Lys Ala Asp Ala
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 11

Lys Ala Asp Ala Lys Ala Asp Ala
1               5

<210> SEQ ID NO 12
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 12

Ala Glu Ala Glu Ala His Ala His Ala Glu Ala Glu Ala His Ala His
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 13

Ala Glu Ala Glu Ala His Ala His
1               5

```
<210> SEQ ID NO 14
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 14

Phe Glu Phe Glu Phe Lys Phe Lys Phe Glu Phe Glu Phe Lys Phe Lys
 1               5                  10                  15

<210> SEQ ID NO 15
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 15

Phe Glu Phe Lys Phe Glu Phe Lys Phe Glu Phe Lys
 1               5                  10

<210> SEQ ID NO 16
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 16

Phe Glu Phe Lys Phe Glu Phe Lys
 1               5

<210> SEQ ID NO 17
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 17

Leu Glu Leu Glu Leu Lys Leu Lys Leu Glu Leu Glu Leu Lys Leu Lys
 1               5                  10                  15

<210> SEQ ID NO 18
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 18

Leu Glu Leu Glu Leu Lys Leu Lys
 1               5

<210> SEQ ID NO 19
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 19

Ala Glu Ala Glu Ala Lys Ala Lys Ala Glu Ala Glu Ala Lys Ala Lys
 1               5                  10                  15
```

```
<210> SEQ ID NO 20
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 20

Ala Glu Ala Glu Ala Glu Ala Glu Ala Lys Ala Lys
 1               5                  10

<210> SEQ ID NO 21
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 21

Ala Glu Ala Glu Ala Lys Ala Lys
 1               5

<210> SEQ ID NO 22
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 22

Lys Ala Lys Ala Lys Ala Lys Ala Glu Ala Glu Ala Glu Ala Glu Ala
 1               5                  10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 23

Ala Glu Ala Glu Ala Glu Ala Glu Ala Lys Ala Lys Ala Lys Ala Lys
 1               5                  10                  15

<210> SEQ ID NO 24
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 24

Lys Leu Asp Leu Lys Leu Asp Leu Lys Leu Asp Leu
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 25

Lys Leu Glu Leu Lys Leu Glu Leu Lys Leu Glu Leu
 1               5                  10

<210> SEQ ID NO 26
```

<211> LENGTH: 16
<212> TYPE: PRT
<213> ORGANISM: Artificial Sequence
<220> FEATURE:
<223> OTHER INFORMATION: Synthetic Peptide

<400> SEQUENCE: 26

Arg Ala Arg Ala Arg Ala Arg Ala Asp Ala Asp Ala Asp Ala Asp Ala
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 27

Ala Asp Ala Asp Ala Asp Ala Asp Ala Arg Ala Arg Ala Arg Ala Arg
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 28

Asp Ala Asp Ala Asp Ala Asp Ala Arg Ala Arg Ala Arg Ala Arg Ala
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 29

Ala Asp Ala Asp Ala Asp Ala Asp Ala Arg Ala Arg Ala Arg Ala Arg
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 30

His Glu His Glu His Lys His Lys His Glu His Glu His Lys His Lys
1               5                   10                  15

<210> SEQ ID NO 31
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 31

His Glu His Glu His Lys His Lys
1               5

<210> SEQ ID NO 32
<211> LENGTH: 20

```
<212> TYPE: PRT
<213> ORGANISM: Artificial Sequence
<220> FEATURE:
<223> OTHER INFORMATION: Synthetic Peptide

<400> SEQUENCE: 32

Val Glu Val Glu Val Glu Val Glu Val Glu Val Glu Val Glu Val Glu
 1               5                   10                  15

Val Glu Val Glu
            20

<210> SEQ ID NO 33
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 33

Arg Phe Arg Phe Arg Phe Arg Phe Arg Phe Arg Phe Arg Phe Arg Phe
 1               5                   10                  15

Arg Phe Arg Phe
            20

<210> SEQ ID NO 34
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 34

Leu Gln Asp Ala Leu Glu Asp Ala Leu Gln Asp Ala Leu Glu Asp Ala
 1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 1
<223> OTHER INFORMATION: Ac-Ala

<400> SEQUENCE: 35

Ala Ala Ala Ala Ala Ala Asp
 1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 1
<223> OTHER INFORMATION: Ac-Val

<400> SEQUENCE: 36

Val Val Val Val Val Val Asp
 1               5

<210> SEQ ID NO 37
<211> LENGTH: 8
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 1
<223> OTHER INFORMATION: Ac-Ala

<400> SEQUENCE: 37

Ala Ala Ala Ala Ala Ala Asp Asp
  1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 1
<223> OTHER INFORMATION: Ac-Val

<400> SEQUENCE: 38

Val Val Val Val Val Val Asp Asp
  1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 1
<223> OTHER INFORMATION: Ac-Leu

<400> SEQUENCE: 39

Leu Leu Leu Leu Leu Leu Asp Asp
  1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 8
<223> OTHER INFORMATION: c-term amidation

<400> SEQUENCE: 40

Lys Lys Ile Ile Ile Ile Ile Ile
  1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 8
<223> OTHER INFORMATION: c-term amidation

<400> SEQUENCE: 41
```

```
Lys Lys Leu Leu Leu Leu Leu Leu
  1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 8
<223> OTHER INFORMATION: c-term amidation

<400> SEQUENCE: 42

Lys Lys Ala Ala Ala Ala Ala Ala
  1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 8
<223> OTHER INFORMATION: c-term amidation

<400> SEQUENCE: 43

Lys Lys Val Val Val Val Val Val
  1               5

<210> SEQ ID NO 44
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 44

Asp Asp Asp Asp Asp Asp Asp Asp Asp Asp Ala Ala Ala Ala Ala Ala
  1               5                  10                  15

Ala Ala Ala Ala
             20

<210> SEQ ID NO 45
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 45

Ala Ala Ala Ala Ala Ala Ala Ala Ala Ala Asp Asp Asp Asp Asp Asp
  1               5                  10                  15

Asp Asp Asp Asp
             20

<210> SEQ ID NO 46
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 46
```

Glu Glu Glu Glu Glu Gly Glu Glu Glu Ala Ala Ala Ala Ala
1               5                   10                  15

Ala Ala Ala Ala
            20

<210> SEQ ID NO 47
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 47

Ala Ala Ala Ala Ala Ala Ala Ala Ala Ala Glu Glu Glu Glu Glu Glu
1               5                   10                  15

Glu Glu Glu Glu
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 48

Asp Asp Asp Asp Asp Asp Asp Asp Asp Val Val Val Val Val Val
1               5                   10                  15

Val Val Val Val
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 49

Val Val Val Val Val Val Val Val Val Val Asp Asp Asp Asp Asp Asp
1               5                   10                  15

Asp Asp Asp Asp
            20

<210> SEQ ID NO 50
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 50

Asp Asp Asp Asp Asp Asp Asp Asp Asp Asp Pro Pro Pro Pro Pro Pro
1               5                   10                  15

Pro Pro Pro Pro
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 51

Pro Pro Pro Pro Pro Pro Pro Pro Pro Pro Asp Asp Asp Asp Asp Asp
1               5                   10                  15

Asp Asp Asp Asp
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 52

Ala Ala Ala Ala Ala Ala Ala Ala Ala Ala His His His His His His
1               5                   10                  15

His His His His
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 53

His His His His His His His His His His Ala Ala Ala Ala Ala Ala
1               5                   10                  15

Ala Ala Ala Ala
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 54

Lys Lys Lys Lys Lys Lys Lys Lys Lys Lys Ala Ala Ala Ala Ala Ala
1               5                   10                  15

Ala Ala Ala Ala
            20

<210> SEQ ID NO 55
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 55

Ala Ala Ala Ala Ala Ala Ala Ala Ala Ala Lys Lys Lys Lys Lys Lys
1               5                   10                  15

Lys Lys Lys Lys
            20

<210> SEQ ID NO 56
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 56

Arg Arg Arg Arg Arg Arg Arg Arg Arg Ala Ala Ala Ala Ala
1               5                   10                  15

Ala Ala Ala Ala
        20

<210> SEQ ID NO 57
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 57

Ala Ala Ala Ala Ala Ala Ala Ala Ala Arg Arg Arg Arg Arg Arg
1               5                   10                  15

Arg Arg Arg Arg
        20

<210> SEQ ID NO 58
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 58

Asp Asp Asp Asp Asp Asp Asp Asp Asp Ala Ala Ala Ala Ala Ala
1               5                   10                  15

Ala Ala Ala Ala Asp Asp Asp Asp Asp Asp Asp Asp Asp
        20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 59

Ala Ala Ala Ala Ala Ala Ala Ala Ala Asp Asp Asp Asp Asp Asp
1               5                   10                  15

Asp Asp Asp Asp Ala Ala Ala Ala Ala Ala Ala Ala Ala
        20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 60

Glu Glu Glu Glu Glu Glu Glu Glu Glu Ala Ala Ala Ala Ala Ala
1               5                   10                  15

Ala Ala Ala Ala Glu Glu Glu Glu Glu Glu Glu Glu Glu
        20                  25                  30

<210> SEQ ID NO 61
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 61

Ala Ala Ala Ala Ala Ala Ala Ala Glu Glu Glu Glu Glu Glu Glu
1               5                   10                  15

Glu Glu Glu Glu Ala Ala Ala Ala Ala Ala Ala Ala Ala Ala Ala
                20                  25                  30

<210> SEQ ID NO 62
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 62

Asp Asp Asp Asp Asp Asp Asp Asp Asp Val Val Val Val Val Val
1               5                   10                  15

Val Val Val Val Asp Asp Asp Asp Asp Asp Asp Asp Asp
                20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 63

Val Val Val Val Val Val Val Val Val Asp Asp Asp Asp Asp Asp
1               5                   10                  15

Asp Asp Asp Asp Val Val Val Val Val Val Val Val Val
                20                  25                  30

<210> SEQ ID NO 64
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 64

Asp Asp Asp Asp Asp Asp Asp Asp Asp Asp Pro Pro Pro Pro Pro
1               5                   10                  15

Pro Pro Pro Pro Asp Asp Asp Asp Asp Asp Asp Asp Asp Asp
                20                  25                  30

<210> SEQ ID NO 65
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 65

Pro Pro Pro Pro Pro Pro Pro Pro Pro Asp Asp Asp Asp Asp Asp
1               5                   10                  15

Asp Asp Asp Asp Pro Pro Pro Pro Pro Pro Pro Pro Pro
                20                  25                  30

<210> SEQ ID NO 66
<211> LENGTH: 30
<212> TYPE: PRT
<213> ORGANISM: Artificial Sequence
<220> FEATURE:

<223> OTHER INFORMATION: Synthetic Peptide

<400> SEQUENCE: 66

Ala Ala Ala Ala Ala Ala Ala Ala Ala Ala His His His His His
1               5                   10                  15

His His His His Ala Ala Ala Ala Ala Ala Ala Ala Ala Ala
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 67

His His His His His His His His His Ala Ala Ala Ala Ala Ala
1               5                   10                  15

Ala Ala Ala Ala His His His His His His His His His
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 68

Lys Lys Lys Lys Lys Lys Lys Lys Lys Ala Ala Ala Ala Ala Ala
1               5                   10                  15

Ala Ala Ala Ala Lys Lys Lys Lys Lys Lys Lys Lys Lys Lys
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 69

Ala Ala Ala Ala Ala Ala Ala Ala Ala Ala Lys Lys Lys Lys Lys
1               5                   10                  15

Lys Lys Lys Lys Ala Ala Ala Ala Ala Ala Ala Ala Ala
            20                  25                  30

<210> SEQ ID NO 70
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 70

Arg Arg Arg Arg Arg Arg Arg Arg Arg Ala Ala Ala Ala Ala Ala
1               5                   10                  15

Ala Ala Ala Ala Arg Arg Arg Arg Arg Arg Arg Arg Arg Arg
            20                  25                  30

<210> SEQ ID NO 71
<211> LENGTH: 30
<212> TYPE: PRT
<213> ORGANISM: Artificial Sequence

```
<220> FEATURE:
<223> OTHER INFORMATION: Synthetic Peptide

<400> SEQUENCE: 71

Ala Ala Ala Ala Ala Ala Ala Ala Ala Arg Arg Arg Arg Arg Arg
 1               5                  10                  15

Arg Arg Arg Arg Ala Ala Ala Ala Ala Ala Ala Ala
             20                  25                  30

<210> SEQ ID NO 72
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 72

Lys Lys Lys Lys Lys Lys Lys Lys Lys Lys Ala Ala Ala Ala Ala
 1               5                  10                  15

Ala Ala Ala Ala Asp Asp Asp Asp Asp Asp Asp Asp Asp
             20                  25                  30

<210> SEQ ID NO 73
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 73

Lys Lys Lys Lys Lys Lys Lys Lys Lys Lys Ala Ala Ala Ala Ala
 1               5                  10                  15

Ala Ala Ala Ala Glu Glu Glu Glu Glu Glu Glu Glu Glu
             20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 74

Arg Arg Arg Arg Arg Arg Arg Arg Arg Arg Val Val Val Val Val
 1               5                  10                  15

Val Val Val Val Asp Asp Asp Asp Asp Asp Asp Asp Asp
             20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 75

Lys Lys Lys Lys Lys Lys Lys Lys Lys Lys Pro Pro Pro Pro Pro
 1               5                  10                  15

Pro Pro Pro Pro Asp Asp Asp Asp Asp Asp Asp Asp Asp
             20                  25                  30

<210> SEQ ID NO 76
<211> LENGTH: 30
<212> TYPE: PRT
```

-continued

```
<213> ORGANISM: Artificial Sequence
<220> FEATURE:
<223> OTHER INFORMATION: Synthetic Peptide

<400> SEQUENCE: 76

His His His His His His His His His His Ala Ala Ala Ala Ala Ala
1               5                   10                  15

Ala Ala Ala Ala Glu Glu Glu Glu Glu Glu Glu Glu Glu Glu
            20                  25                  30
```